United States Patent
Kawarabata et al.

(10) Patent No.: US 7,651,473 B2
(45) Date of Patent: Jan. 26, 2010

(54) EXTRACORPOREAL BLOOD CIRCULATING APPARATUS, CLOSED-TYPE VENOUS RESERVOIR AND EXTRACORPOREAL BLOOD CIRCULATING METHOD

(75) Inventors: Shigeki Kawarabata, Hiroshima (JP); Hiroyuki Maeda, Hiroshima (JP); Yutaka Nakahara, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 527 days.

(21) Appl. No.: 10/581,732

(22) PCT Filed: Dec. 8, 2004

(86) PCT No.: PCT/JP2004/018303

§ 371 (c)(1),
(2), (4) Date: Sep. 6, 2006

(87) PCT Pub. No.: WO2005/056082

PCT Pub. Date: Jun. 23, 2005

(65) Prior Publication Data

US 2007/0100273 A1    May 3, 2007

(30) Foreign Application Priority Data

Dec. 10, 2003  (JP)  ............................. 2003-412192
Sep. 17, 2004  (JP)  ............................. 2004-271780

(51) Int. Cl.
*A61M 37/00* (2006.01)
(52) U.S. Cl. ..................................... 604/6.15; 604/6.09
(58) Field of Classification Search ................ 604/6.15, 604/6.09, 403, 6.11
See application file for complete search history.

(56) References Cited

U.S. PATENT DOCUMENTS 3,907,504 A * 9/1975 Hammond et al. ............ 422/46

(Continued)

FOREIGN PATENT DOCUMENTS

EP    1 053 760    11/2000

(Continued)

*Primary Examiner*—Leslie R Deak
(74) *Attorney, Agent, or Firm*—Hamre, Schumann, Mueller & Larson, P.C.

(57) ABSTRACT

The extracorporeal blood circulating apparatus of the present invention includes: a closed-type venous reservoir having a blood storage chamber and a volume adjusting chamber that are disposed adjacently by partitioning a closed space formed by a housing; an adjusting liquid tank for storing an adjusting liquid that is connected to the volume adjusting chamber; and a blood pump that is connected to the blood storage chamber. In the housing, an inflow port for allowing blood to inflow and an outflow port for allowing blood to outflow are provided so as to communicate with the blood storage chamber, and an adjusting port for injecting and ejecting the adjusting liquid is provided so as to communicate with the volume adjusting chamber. The blood pump is connected via the outflow port, and the adjusting liquid tank is connected via the adjusting port. The closed space is partitioned by a flexible septum member so as to form the blood storage chamber and the volume adjusting chamber, and the adjusting liquid tank and the adjusting port are connected by a conduit member having a configuration that can adjust a flowing amount. Control of a blood storage amount to be most appropriate and easy adjustment are possible throughout all steps from before starting an extracorporeal blood circulation to terminating it.

19 Claims, 11 Drawing Sheets

U.S. PATENT DOCUMENTS

| | | | | |
|---|---|---|---|---|
| 4,573,992 A | * | 3/1986 | Marx | 604/408 |
| 4,772,256 A | * | 9/1988 | Lane et al. | 604/6.09 |
| 4,976,707 A | * | 12/1990 | Bodicky et al. | 604/408 |
| 5,683,357 A | * | 11/1997 | Magram | 604/8 |
| 6,287,270 B1 | | 9/2001 | Fini | |

FOREIGN PATENT DOCUMENTS

| | | | |
|---|---|---|---|
| JP | 52-120593 | | 10/1977 |
| JP | 62-27965 | | 2/1987 |
| JP | 2000-000299 | * | 1/2000 |
| JP | 2000-299 | | 1/2000 |

\* cited by examiner

EXTRACORPOREAL BLOOD CIRCULATING APPARATUS, CLOSED-TYPE VENOUS RESERVOIR AND EXTRACORPOREAL BLOOD CIRCULATING METHOD

TECHNICAL FIELD

The present invention relates to an extracorporeal blood circulating apparatus utilizing a closed-type venous reservoir that is used for storing blood temporarily for a surgical operation on a cardiocirculatory system requiring an extracorporeal circulation, a configuration of the closed-type venous reservoir and an extracorporeal blood circulating method.

BACKGROUND ART

In a surgical operation on a cardiocirculatory system that requires an extracorporeal circulation, for the purposes of obtaining a bloodless operative field of view and achieving a manipulation of the surgical operation simply, a venous reservoir generally is used in an extracorporeal circulation circuit for temporarily storing blood from a body. Recently, recognition of less invasive surgical operations has been increased, so that an extracorporeal circulation system with a small incursion into the blood has been required.

Generally used venous reservoirs are roughly divided into: open-type venous reservoirs having hard outer shells; and flexible closed-type venous reservoirs that have flexible outer shells and are closed. The open-type venous reservoir is excellent in a function of removing air bubbles that are mixed into blood, and can show a blood storage capacity precisely. However, the open-type venous reservoir exposes blood to outside air, which is likely to cause an effect on the blood such as blood coagulation. On the other hand, the flexible closed-type venous reservoir basically does not expose blood to outside air, which causes a smaller effect on the blood. However, the flexible closed-type venous reservoir has problems of difficulty of showing its blood storage capacity, removing air bubbles and the like. An example of the closed-type venous reservoir having a means for solving these problems is disclosed in Patent Document 1.

In the dosed-type venous reservoir, a closed space is formed by an outer wall that forms a housing of the venous reservoir. A septum member made of a flexible material is provided in the outer wall, and the closed space is partitioned by the septum member into a blood storage chamber and a volume adjusting chamber. In the blood storage chamber, an inflow port and an outflow port are provided. The inflow port is used for introducing blood, and the outflow port is used for ejecting blood. In the volume adjusting chamber, an adjusting port is provided, which is used for injecting and ejecting an adjusting liquid for volume adjustment.

By injecting and ejecting the adjusting liquid for the volume adjustment with respect to the volume adjusting chamber through the adjusting port, an amount of the adjusting liquid to be stored in the volume adjusting chamber is changed. Thereby, the septum member is moved, thus changing the volume of the volume adjusting chamber, and accordingly, changing the capacity of the blood storage chamber. In addition, the volume of the volume adjusting chamber can be known by measuring a transferring amount of the adjusting liquid.

Patent document 1: JP 2000-299 A

DISCLOSURE OF INVENTION

Problem to be Solved by the Invention

As described above, the dosed-type venous reservoir having the hard outer shell has various advantages of enabling the easy measurement and the control of the blood storage capacity and the like.

For example, the dosed-type venous reservoir can decrease the blood storage capacity to be sufficiently small. The reason for this is because, even when the blood storage capacity is small, the configuration of the dosed-type venous reservoir does not allow the blood storage amount to be zero and does not mix air into the circulating blood, and thus the blood storage capacity can be decreased safely. On the other hand, in the case of the open-type venous reservoir, when the blood storage capacity is small, the blood storage amount may be zero, which may cause air to be mixed into the circulating blood.

Moreover, in the case of the closed-type venous reservoir, by controlling a filling amount of the adjusting liquid into the volume adjusting chamber, the blood storage capacity can be controlled directly and forcibly. Accordingly, if the filling amount of the adjusting liquid into the volume adjusting chamber is kept constant, the blood storage capacity can be kept constant. On the other hand, in the case of the open-type venous reservoir, it actually is possible to change the blood storage capacity by changing a rotational speed of a blood pump, but it is difficult to control the blood storage amount directly. The reason for this is that the blood storage capacity actually is not determined only by the rotational speed of the blood pump, but is affected also by other conditions such as resistance of a blood channel.

However, the extracorporeal blood circulating apparatus using the conventional dosed-type venous reservoir is not considered to have an appropriate configuration for sufficiently utilizing the above-described characteristics of the dosed-type venous reservoir.

The present invention intends to provide an extracorporeal blood circulating apparatus that easily can adjust a blood storage amount to be most appropriate in each step of an extracorporeal circulation with a simple configuration, by sufficiently utilizing the characteristics of the dosed-type venous reservoir that is capable of easy measurement and direct and forcible control of a blood storage capacity. In addition, the present invention intends to provide a dosed-type venous reservoir to be used for the extracorporeal blood circulating apparatus, and moreover, to provide an extracorporeal blood circulating method using the same.

Means for Solving Problem

The extracorporeal blood circulating apparatus of the present invention includes: a closed-type venous reservoir having a blood storage chamber for storing blood and a volume adjusting chamber for storing an adjusting liquid for volume adjustment that are disposed adjacently by partitioning a closed space formed by a housing; an adjusting liquid tank for storing the adjusting liquid that is connected to the volume adjusting chamber; and a blood pump that is connected to the blood storage chamber. The housing is provided with an inflow port for allowing blood to inflow and an outflow port for allowing blood to outflow that respectively communicate with the blood storage chamber, and an adjusting port for injecting and ejecting the adjusting liquid that communicates with to the volume adjusting chamber, the blood pump is connected to the blood storage chamber via the outflow port, and the adjusting liquid tank being connected to the volume adjusting chamber via the adjusting port. The closed space of the closed-type venous reservoir is partitioned by a flexible septum member so as to form the blood storage chamber and the volume adjusting chamber, and the adjusting liquid tank and the adjusting port are connected by a conduit member having a configuration that can adjust a flowing amount.

The closed-type venous reservoir of the present invention includes: a housing forming a closed space; a blood storage chamber for storing blood and a volume adjusting chamber for storing an adjusting liquid for volume adjustment that are disposed adjacently by partitioning the closed space; an inflow port for allowing blood to inflow and an outflow port for allowing blood to outflow that are provided at the housing so as to communicate with the blood storage chamber; and an adjusting port for injecting and ejecting the adjusting liquid that is provided at the housing so as to communicate with to the volume adjusting chamber. The closed space is partitioned by a flexible septum member into the blood storage chamber and the volume adjusting chamber, a first blockade avoiding channel forming a space bulging outward is provided on an inner wall surface of the housing at a part facing the blood storage chamber; and the inflow port and the outflow port are disposed so as to communicate with the first blockade avoiding channel.

The extracorporeal blood circulating method of the present invention includes: using the extracorporeal blood circulating apparatus with the above-described configuration; connecting the inflow port of the closed-type venous reservoir to a blood removal part of an living body directly or via another member; connecting an outlet of the blood pump to an autotransfusing part of the living body directly or via another member; filling a system including the adjusting liquid tank, the conduit and the volume adjusting chamber with the adjusting liquid; adjusting a filling amount of the adjusting liquid in the volume adjusting chamber by adjusting a height of the adjusting liquid tank with respect to the closed-type venous reservoir so that the blood storage chamber may have a blood storage capacity appropriate for priming before starting the extracorporeal blood circulation; dosing a channel of the conduit member after completing the adjustment so as to start the priming by operating the blood pump; and releasing the channel of the conduit member and holding the adjusting liquid tank in a position, with respect to the blood removal part of the living body, that is lower than a height of the adjusting liquid tank during the priming so as to start blood removal, after completing the priming.

Effects of the Invention

According to the configuration of the extracorporeal blood circulating apparatus of the present invention or the like, a blood storage capacity can be measured easily and can be tracked in accordance with a pressure change in a circulation path, and thus a buffer action can be obtained. Moreover, the characteristics of the dosed-type venous reservoir that a blood storage capacity is capable of being directly and forcibly controlled as necessary can be utilized sufficiently, and the blood storage amount in each step of an extracorporeal circulation easily can be adjusted to be most appropriate, with a simple configuration.

Figure 1:
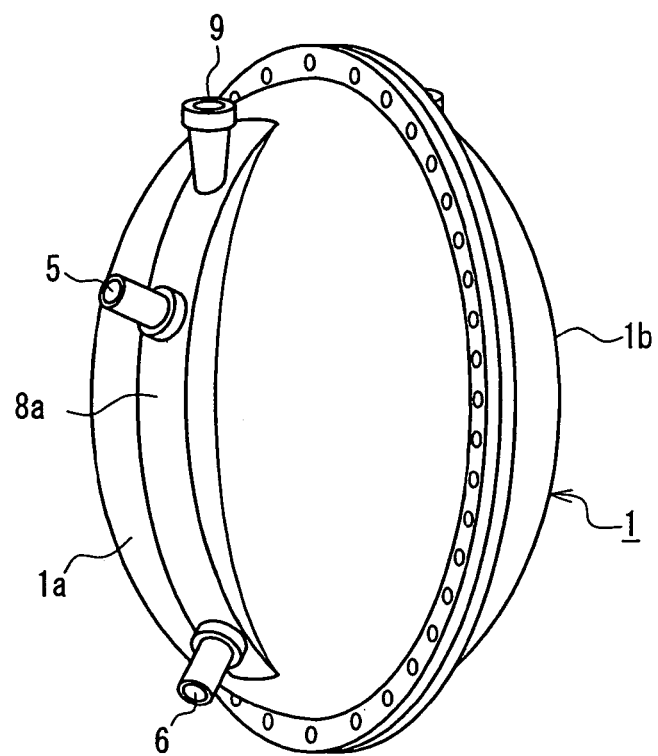
FIG. 1 is a perspective view showing a closed-type venous reservoir according to an embodiment of the present invention.

EXPLANATION OF REFERENCE CODES 1 housing
1a, 1b half
2 septum member
3 blood storage chamber
4 volume adjusting chamber
5 inflow port
6 outflow port
7 adjusting port
8a first blockade avoiding channel
8b second blockade avoiding channel
9 air vent port
10 pressure measuring port
11 gas-liquid separator membrane
20 closed-type venous reservoir
21 adjusting liquid tank
21a adjusting liquid
22 blood pump
23 adjusting path tube
24 support
25 blood removal-side tube
26 autotransfusion-side tube
27, 28 clamp
29 fine-adjusting port
30 syringe
31 auxiliary venous reservoir
32 pump
33 auxiliary system tube

DESCRIPTION OF THE INVENTION

In the extracorporeal blood circulating apparatus of the present invention, the conduit member may be made of a flexible tube. Alternatively, the conduit member may include a channel adjusting portion for changing a channel cross-sectional area in a channel.

It is preferable that the extracorporeal blood circulating apparatus of the present invention includes a measuring portion for measuring an amount of the adjusting liquid that is stored in the adjusting liquid tank.

Moreover, it is preferable that the closed-type venous reservoir includes: a first blockade avoiding channel forming a space bulging outward that is provided on an inner wall surface of the housing at a part facing the blood storage chamber; and the inflow port and the outflow port that respectively are disposed so as to communicate with the first blockade avoiding channel.

Moreover, it is preferable that the extracorporeal blood circulating apparatus of the present invention includes a fine-adjusting port for injecting and ejecting the adjusting liquid between the adjusting port and the adjusting liquid tank.

Moreover, the extracorporeal blood circulating apparatus of the present invention can include: an auxiliary venous reservoir for collecting blood that is removed from parts other than a blood removal part of a living body; and a blood ejecting device for allowing the blood that is stored in the auxiliary venous reservoir to inflow into the inflow port of the closed-type venous reservoir.

Moreover, the extracorporeal blood circulating apparatus of the present invention can include a supporting unit holding the adjusting liquid tank so that a height of the adjusting liquid tank can be varied.

In the closed-type venous reservoir of the present invention, it is preferable that a second blockade avoiding channel forming a space bulging outward is provided on the inner wall surface of the housing at a part facing the volume adjusting chamber, and the adjusting port is disposed so as to communicate with the second blockade avoiding channel.

Moreover, it is preferable that an air vent port is provided so as to communicate with the first blockade avoiding channel.

Moreover, it is preferable that a gas-liquid separator membrane that encloses the inflow port and the air vent port so as to separate the inflow port and the air vent port from the blood storage chamber is disposed at a part where the inflow port is connected to the blood storage chamber.

Moreover, it is preferable that a pressure measuring port is provided so as to communicate with the second blockade avoiding channel.

Moreover, it is preferable that the first blockade avoiding channel is formed into a groove shape along the housing.

The extracorporeal blood circulating method of the present invention further can include: using a flexible tube as the conduit member; and dosing the channel of the conduit member by narrowing a bore of the tube by a clamp.

Moreover, it is possible to change the height of the adjusting liquid tank to be in a higher position with respect to the blood removal part of the living body so as to increase a blood storage capacity of a heart of the living body, during the blood removal.

Moreover, it is possible to decrease a cross-sectional area of a channel that connects the inflow port of the closed-type venous reservoir and the blood removal part of the living body, so as to increase a capacity of a heart of the living body, during the blood removal.

Moreover, it is possible to decrease the height of the adjusting liquid tank with respect to the living body to be lower than the height of the adjusting liquid tank during the blood removal so as to decrease a volume of the blood storage chamber to be sufficient for maintaining a cross-sectional area of a blood channel, operate the blood pump in a state of decreasing an discharging amount, and thereafter terminate the extracorporeal blood circulation.

Moreover, it is possible to provide a fine-adjusting port for injecting and ejecting the adjusting liquid between the adjusting port and the adjusting liquid tank, and inject and eject the adjusting liquid by using a syringe via the fine-adjusting port so as to fine-adjust a filling amount of the adjusting liquid in the volume adjusting chamber.

The extracorporeal blood circulating apparatus according to an embodiment of the present invention will be described below with reference to drawings.

Figure 2:
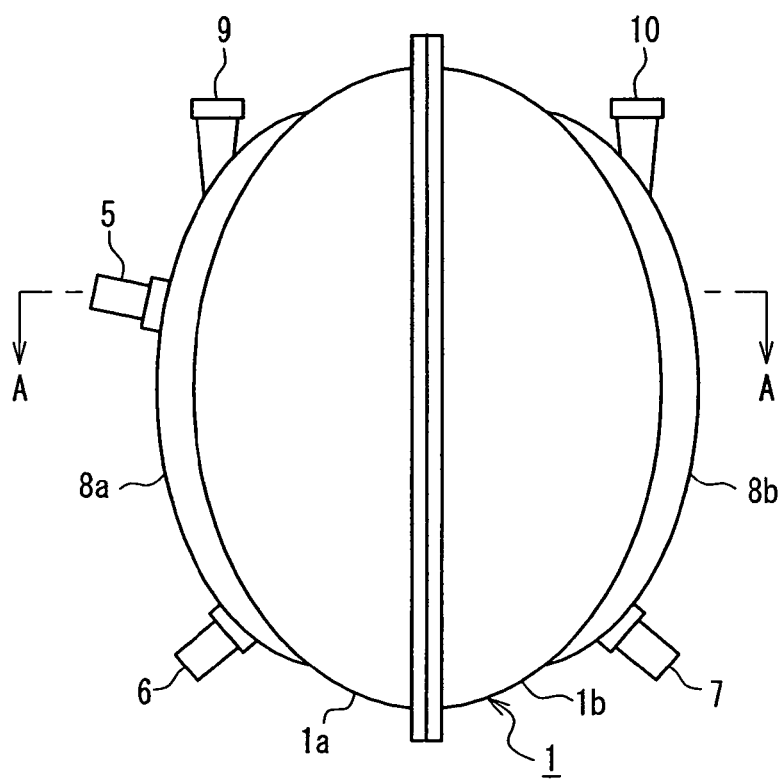
FIG. 2 is a front view showing the dosed-type venous reservoir.
Figure 3A:
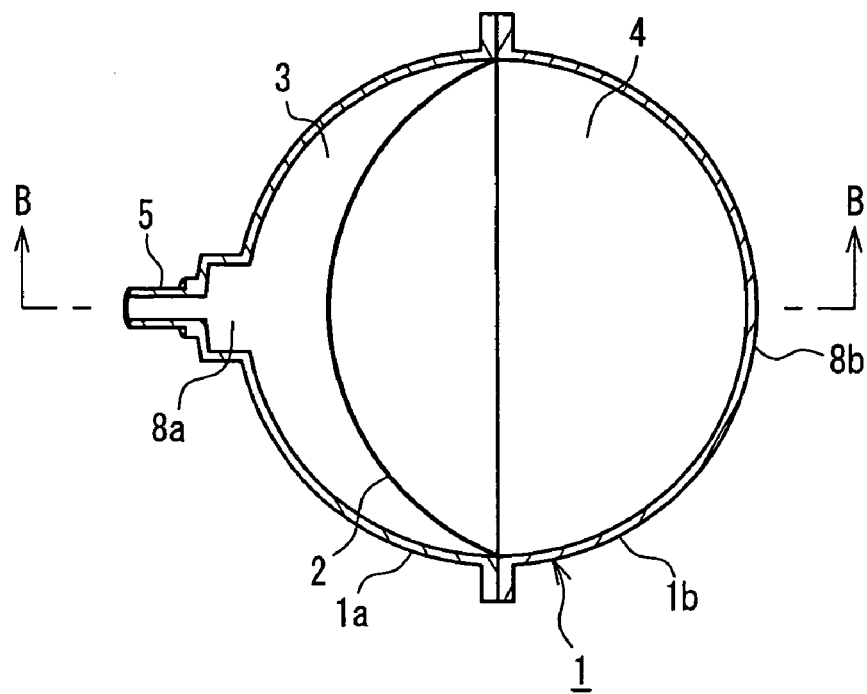
FIG. 3A is a cross-sectional view taken along line A-A of FIG. 2.
Figure 3B:
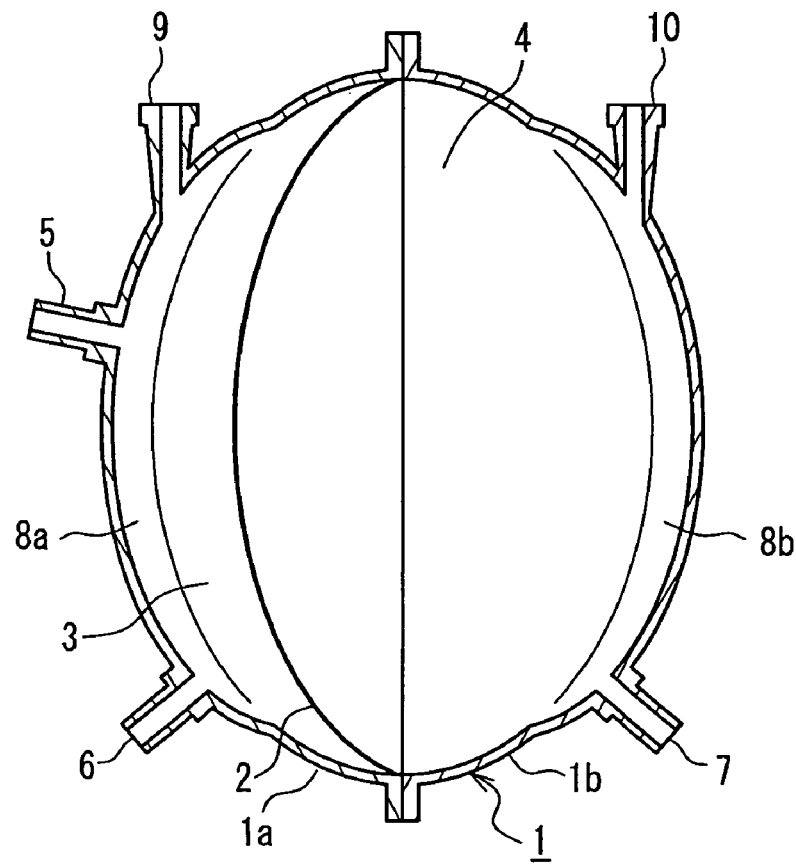
FIG. 3B is a cross-sectional view taken along line B-B of FIG. 3A.

Firstly, a configuration of a dosed-type venous reservoir composing the extracorporeal blood circulating apparatus of the present invention will be described with reference to FIGS. 1 to 4. FIG. 1 is a perspective view showing the dosed-type venous reservoir according to the present embodiment. FIG. 2 is a front view of the dosed-type venous reservoir. FIG. 3A is a cross-sectional view taken along line A-A of FIG. 2, and FIG. 3B is a cross-sectional view taken along line B-B of FIG. 3A.

This closed-type venous reservoir includes a housing 1 made of a hard shell for forming a dosed space, as shown in FIGS. 1 and 2. The housing 1 is formed by combining two halves 1a and 1b, each of which has an outer wall made of a curved surface such as a part of a spherical surface or a spheroid. As shown in FIGS. 3A and 3B, in an internal space of the housing 1, a flexible septum member 2 made of a flexible material is provided, by which a bore is partitioned into a blood storage chamber 3 and a volume adjusting chamber 4. The blood storage chamber 3 is used for temporarily storing blood, and the volume adjusting chamber 4 is used for storing an adjusting liquid for volume adjustment, which are separated by the septum member 2 so as not to be in contact with each other.

On the outer wall of the housing 1 at a part facing the blood storage chamber 3, an inflow port 5 and an outflow port 6 are provided so that they may communicate with the blood storage chamber 3. The inflow port 5 is used for introducing blood, and the outflow port 6 is used for ejecting blood. On the outer wall of the housing 1 at a part facing the volume adjusting chamber 4, an adjusting port 7 is provided, which is used for injecting and ejecting the adjusting liquid for the volume adjustment.

By injecting or ejecting the adjusting liquid for the volume adjustment with respect to the volume adjusting chamber 4 through the adjusting port 7, an amount of the adjusting liquid that is stored in the volume adjusting chamber 4 is changed so as to move the septum member 2, thereby changing the volume of the volume adjusting chamber 4, and accordingly, changing the capacity of the blood storage chamber 3. Moreover, by maintaining a state that allows the adjusting liquid to be injected or ejected freely with respect to the volume adjusting chamber 4, the septum member 2 is moved in accordance with a pressure change in a blood circulation path that passes through the blood storage chamber 3, thereby obtaining a function of changing the capacity of the blood storage chamber 3 automatically. That is, also by increasing or decreasing a pressure in a conduit in which the adjusting liquid flows, in response to a pressure at a blood removal part of a living body, the capacities of the adjusting chamber and the blood storage chamber can be changed. The volume of the volume adjusting chamber 4 can be measured by measuring a transferring amount of the adjusting liquid, whereby the change of the capacity of the blood storage chamber 3 can be known.

A first blockade avoiding channel 8a is provided along the outer wall of the housing 1 so as to protrude from an outer surface of the outer wall, and the inflow port 5, the outflow port 6 and an air vent port 9 are provided outside the housing 1 at a part corresponding to the first blockade avoiding channel 8a. As shown in FIG. 2, a second blockade avoiding channel 8b is provided on a side opposite to the first blockade avoiding channel 8a, and the adjusting port 7 and a pressure measuring port 10 are provided outside the housing 1 at a part corresponding to the second blockade avoiding channel 8b. By connecting a pressure measuring device to the pressure measuring port 10, a pressure in the circulation system can be measured via the septum member 2, without any contact with blood in the blood storage chamber 3.

The first blockade avoiding channel 8a and the second blockade avoiding channel 8b respectively are disposed in parts facing the blood storage chamber 3 and the volume adjusting chamber 4 on an inner wall surface of the housing 1. Each of the first blockade avoiding channel 8a and the second blockade avoiding channel 8b has a stripe shape with a constant width. Thus, when being viewed from an inside of the blood storage chamber 3 or the volume adjusting chamber 4, each of the first blockade avoiding channel 8a and the second blockade avoiding channel 8b forms a groove that is bulging outward on the inner wall surface of the housing 1.

The inflow port 5, the outflow port 6 and the air vent port 9 that are disposed outside the first blockade avoiding channel 8a communicate with the blood storage chamber 3. The adjusting port 7 and the pressure measuring port 10 that are disposed outside the second blockade avoiding channel 8b communicate with the volume adjusting chamber 4. The inflow port 5 is used for introducing blood, and the outflow port 6 is used for ejecting blood. The air vent port 9 is provided to remove air bubbles. The adjusting port 7 is used for injecting and ejecting the adjusting liquid.

Figure 4:
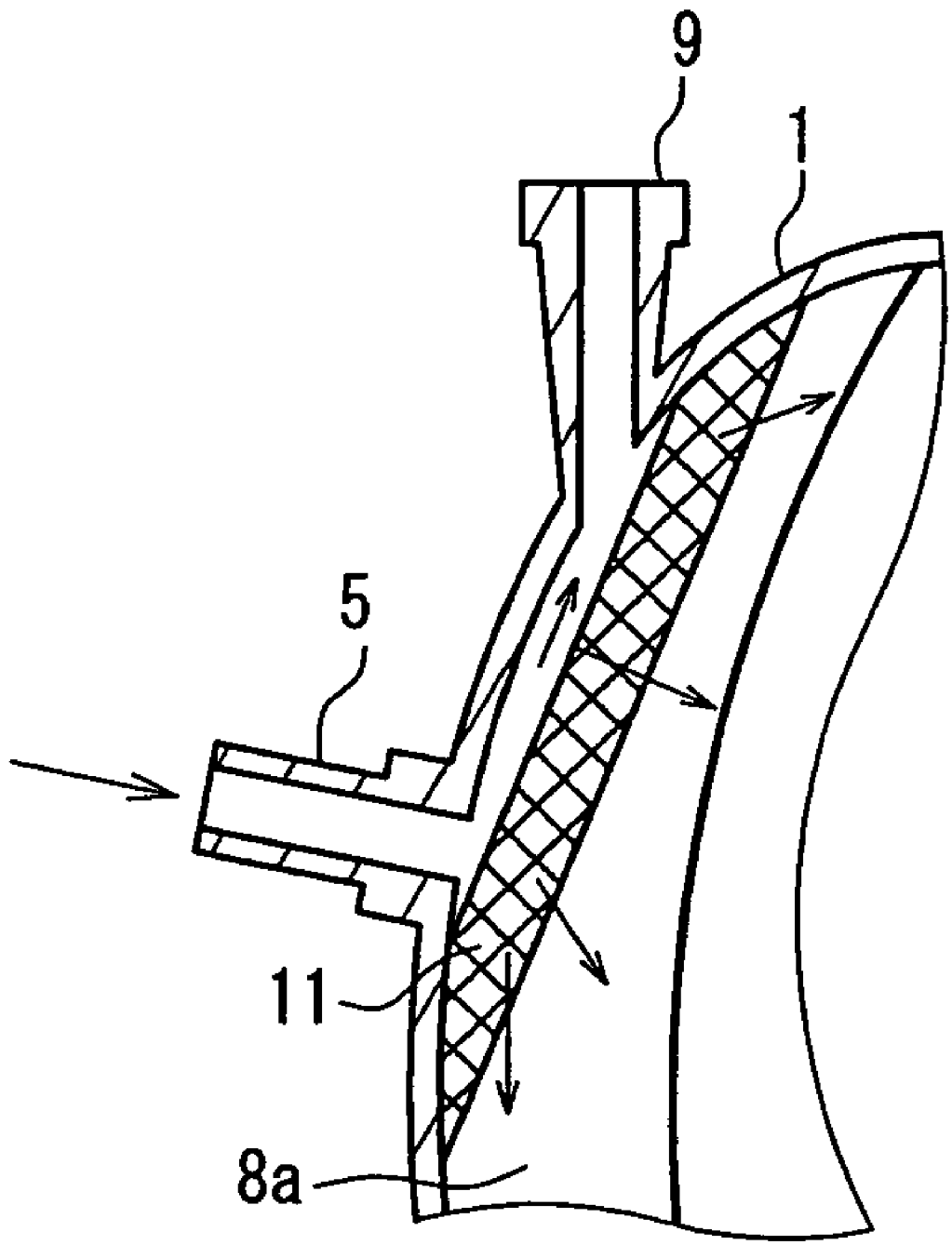
FIG. 4 is an enlarged cross-sectional view showing a relevant part of FIG. 3B.

FIG. 4 is an enlarged view showing a vicinity of the inflow port 5 and the air vent port 9 in FIG. 3B. A gas-liquid separator membrane 11 is disposed in a part where the inflow port 5 communicates with the blood storage chamber 3, which is omitted from FIG. 3B though. By enclosing the inflow port 5 and the air vent port 9 with the gas-liquid separator membrane 11 so as to separate them from the blood storage chamber 3, air bubbles mixed into blood can be removed, and the air bubbles and the blood effectively can be separated from each other.

Functions of the first blockade avoiding channel 8a and the second blockade avoiding channel 8b will be described. When keeping the adjusting liquid to flow into the blood storage chamber 3 and the volume adjusting chamber 4, the septum member 2 is pushed by the flow and deformed freely due to its flexibility, whereby a force may cause the septum member 2 to be sucked into the outflow port 6. However, since the first blockade avoiding channel 8a is provided along the housing 1, the septum member 2 is supported by the inner wall surface of the housing 1 around the first blockade avoiding channel 8a. Therefore, the outflow port 6 is prevented from being blocked by the septum member 2, and a space around the outflow port 6 that is formed by the first blockade avoiding channel 8a is secured as a channel for allowing blood to flow therethrough. The second blockade avoiding channel 8b gives a similar effect so as to prevent the adjusting port 7 from being blocked by the septum member 2. Herein, the second blockade avoiding channel 8b is not necessarily provided, and a practical effect sufficiently can be obtained, by only providing the first blockade avoiding channel 8a.

Figure 5:
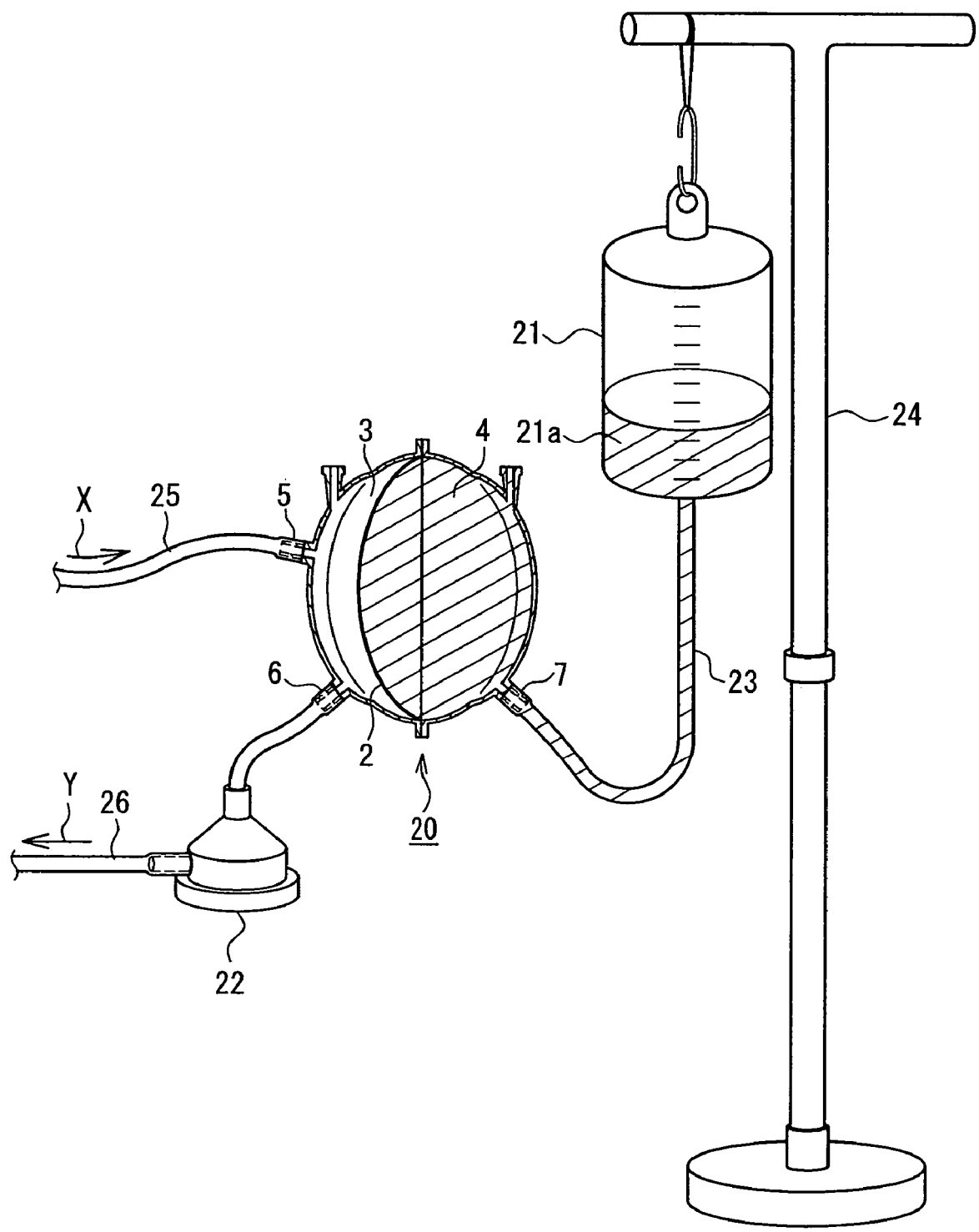
FIG. 5 is a perspective view showing an extracorporeal blood circulating apparatus using the closed-type venous reservoir.

FIG. 5 shows a configuration of the extracorporeal blood circulating apparatus according to the present embodiment, which is configured using the closed-type venous reservoir having the above-described configuration. This extracorporeal blood circulating apparatus includes a closed-type venous reservoir 20 with the above-described configuration, an adjusting liquid tank 21, and a blood pump 22 composed of a centrifugal pump and the like. The adjusting liquid tank 21 is connected to the adjusting port 7 of the closed-type venous reservoir 20 by a flexible adjusting path tube 23 that is a conduit member. An inlet of the blood pump 22 is connected to the outflow port 6 of the closed-type venous reservoir 20. The adjusting liquid tank 21 is supported by a support 24, and a relative height of the adjusting liquid tank 21 with respect to the closed-type venous reservoir 20 can be adjusted. A flexible blood removal-side tube 25 for being connected to a blood removal part of a living body is connected to the inflow port 5 of the closed-type venous reservoir 20, in which blood flows in a direction shown by an arrow X. A flexible autotransfusion-side tube 26 for being connected to an autotransfusing part is connected to an outlet of the blood pump 22, in which blood flows in a direction shown by an arrow Y The adjusting liquid tank 21 has a function of storing an adjusting liquid 21a that is injected and ejected with respect to the volume adjusting chamber 4 of the closed-type venous reservoir 20. The adjusting path tube 23 is configured so that its channel cross-sectional area can be varied. For example, if the adjusting path tube 23 is made of a flexible tube, the channel can be closed, opened or partly closed by narrowing the tube by using a clamp so as to vary the channel cross-sectional area. Alternatively, the adjusting path tube 23 may have a configuration that includes a channel adjusting member for varying the channel cross-sectional area such as a cock in the channel thereof.

Moreover, the adjusting liquid tank 21 includes a measuring portion, for example, a scale, for measuring an amount of the adjusting liquid 21a stored therein.

By changing a position of supporting the adjusting liquid tank 21 by the support 24, a height of the adjusting liquid tank 21 with respect to the blood removal part of the living body, that is, a difference in height of the adjusting liquid 21a is adjusted, whereby an amount of the adjusting liquid 21a stored in the volume adjusting chamber 4 can be increased or decreased. Thereby, the septum member 2 is moved, so that the capacity of the blood storage chamber 3 is adjusted. If the volume of the volume adjusting chamber 4 before starting the blood storage is measured previously, a change of the capacity of the blood storage chamber 3 can be known from a change of the volume of the volume adjusting chamber 4. The change of the volume of the volume adjusting chamber 4 can be measured by a change of an amount of the adjusting liquid 21a that is stored in the adjusting liquid tank 21.

An extracorporeal blood circulating method using this extracorporeal blood circulating apparatus will be described with reference to FIGS. 6 to 10. Herein, the dosed-type venous reservoir 20 is shown in cross section for easy interpretation. In addition, while carrying out an extracorporeal blood circulation, other devices such as an artificial lung, a blood filter and the like also are connected to the circulation path, but they are omitted from the figures.

Figure 6:
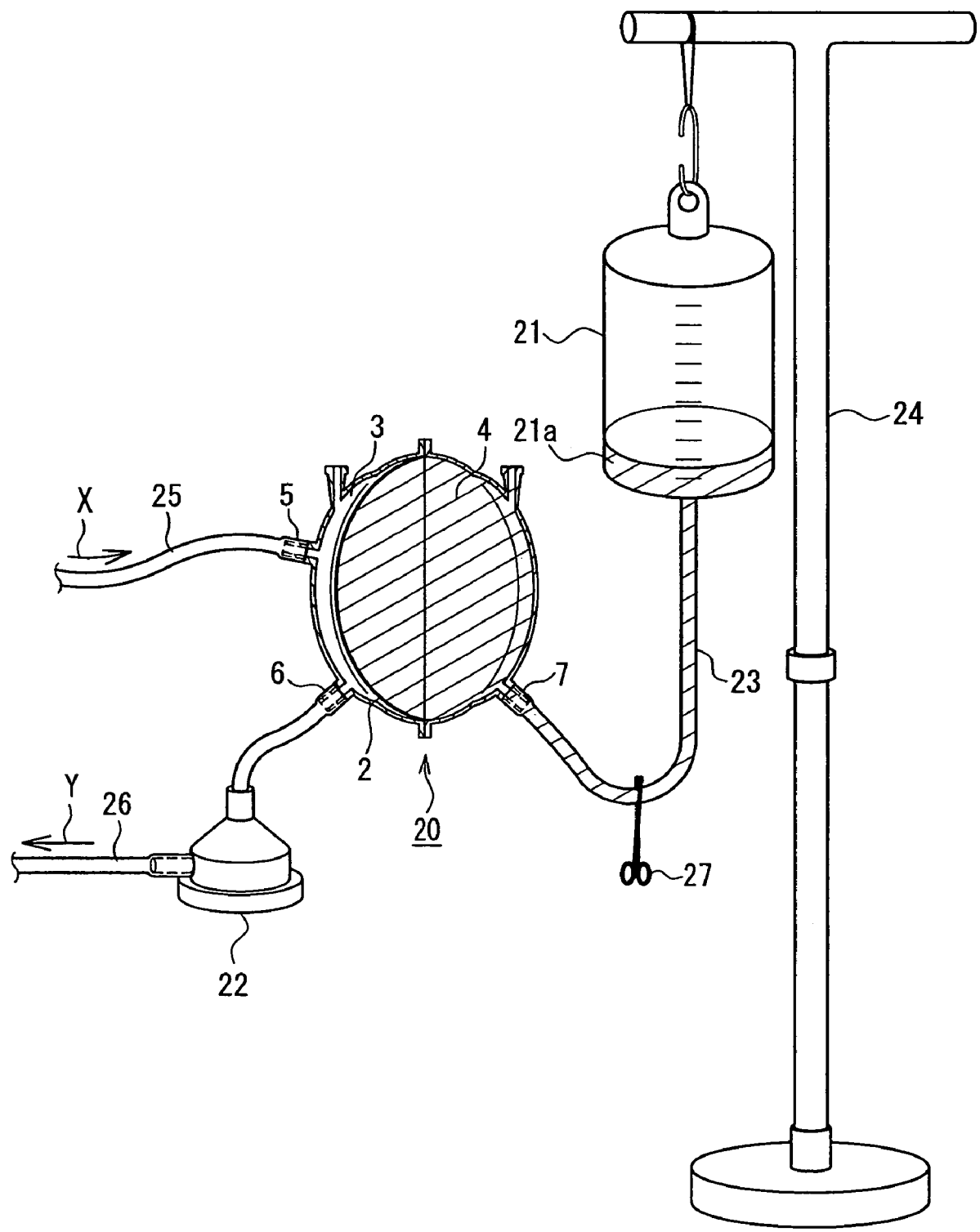
FIG. 6 is a perspective view showing an action of the extracorporeal blood circulating apparatus before starting an extracorporeal blood circulation.

Firstly, operational processes and actions before starting the extracorporeal blood circulation will be described with reference to FIG. 6. When using this closed-type venous reservoir 20, an appropriate amount of, for example, a physiological saline solution as the adjusting liquid 21a is filled in a system including the volume adjusting chamber 4 and the adjusting liquid tank 21. Before starting the extracorporeal blood circulation, the adjusting liquid tank 21 is disposed in a high position so as to fill the volume adjusting chamber 4 with the adjusting liquid 21a sufficiently, thereby adjusting the volume adjusting chamber 4 to have substantially the maximum volume. Thereby, the septum member 2 may be in contact with the inner wall surface of the housing 1 that faces the blood storage chamber 3. Herein, the adjustment is performed so that a minimum channel including the first blockade avoiding channel 8a, that is, a channel cross-sectional area required for priming that will be carried out subsequently, is secured in the blood storage chamber 3. In this state, the adjusting path tube 23 is blocked with the damp 27. An extracorporeal circulation system including the thus formed blood storage chamber 3 that functions with the minimum capacity is filled with a priming solution.

Figure 7:
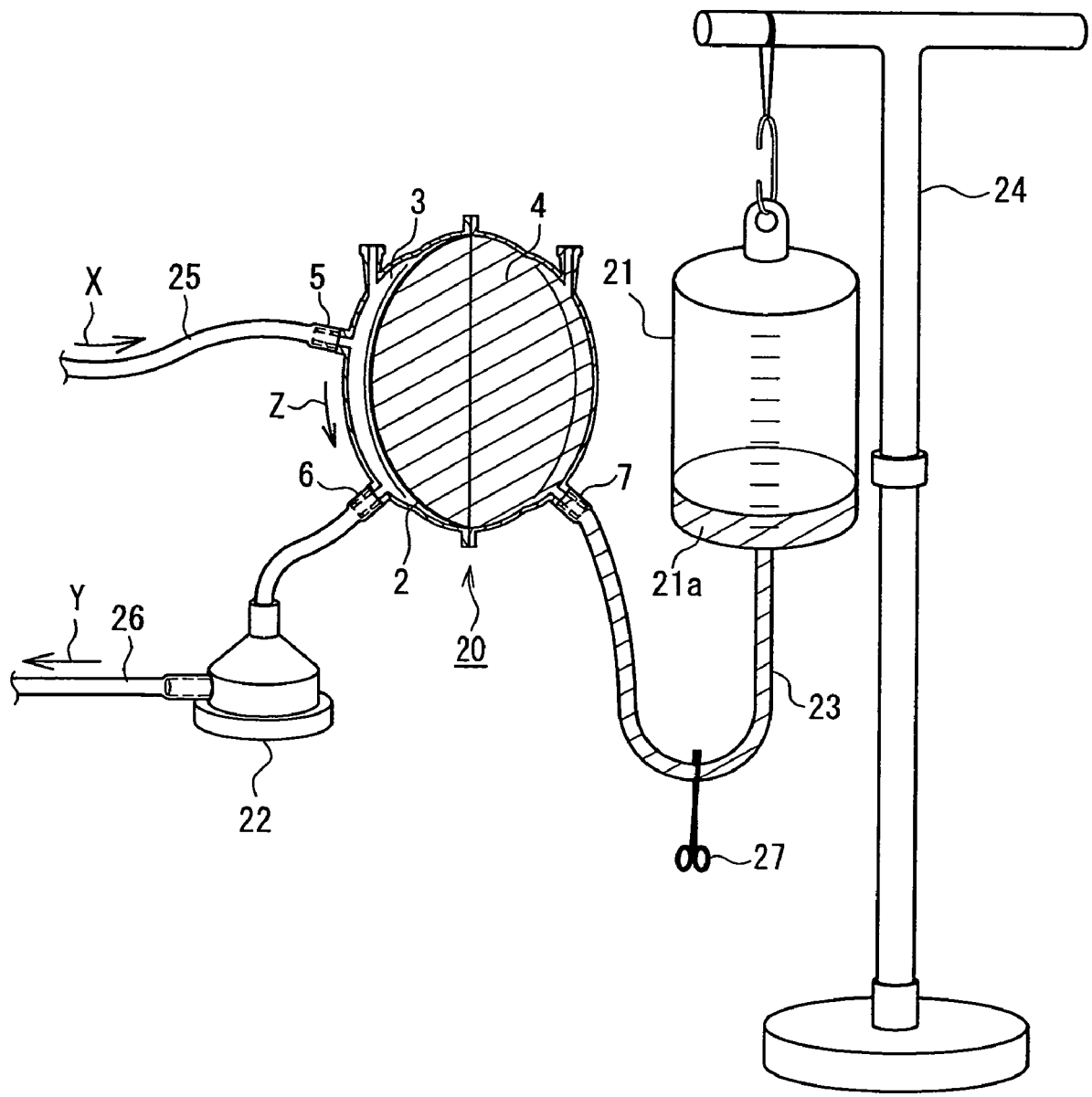
FIG. 7 is a perspective view showing an action of the extracorporeal blood circulating apparatus when starting the extracorporeal blood circulation.

Next, operational processes and actions when starting the extracorporeal blood circulation will be described with reference to FIG. 7. Firstly, the adjusting liquid tank 21 is disposed in a position, with respect to the closed-type venous reservoir 20, that is lower than the position of the adjusting liquid tank 21 in the case of FIG. 6. An operation of the blood pump 22 is started in this state, then the extracorporeal blood circulation is started with the blood flowing through the blood storage chamber 3 in a direction shown by an arrow Z.

Figure 8:
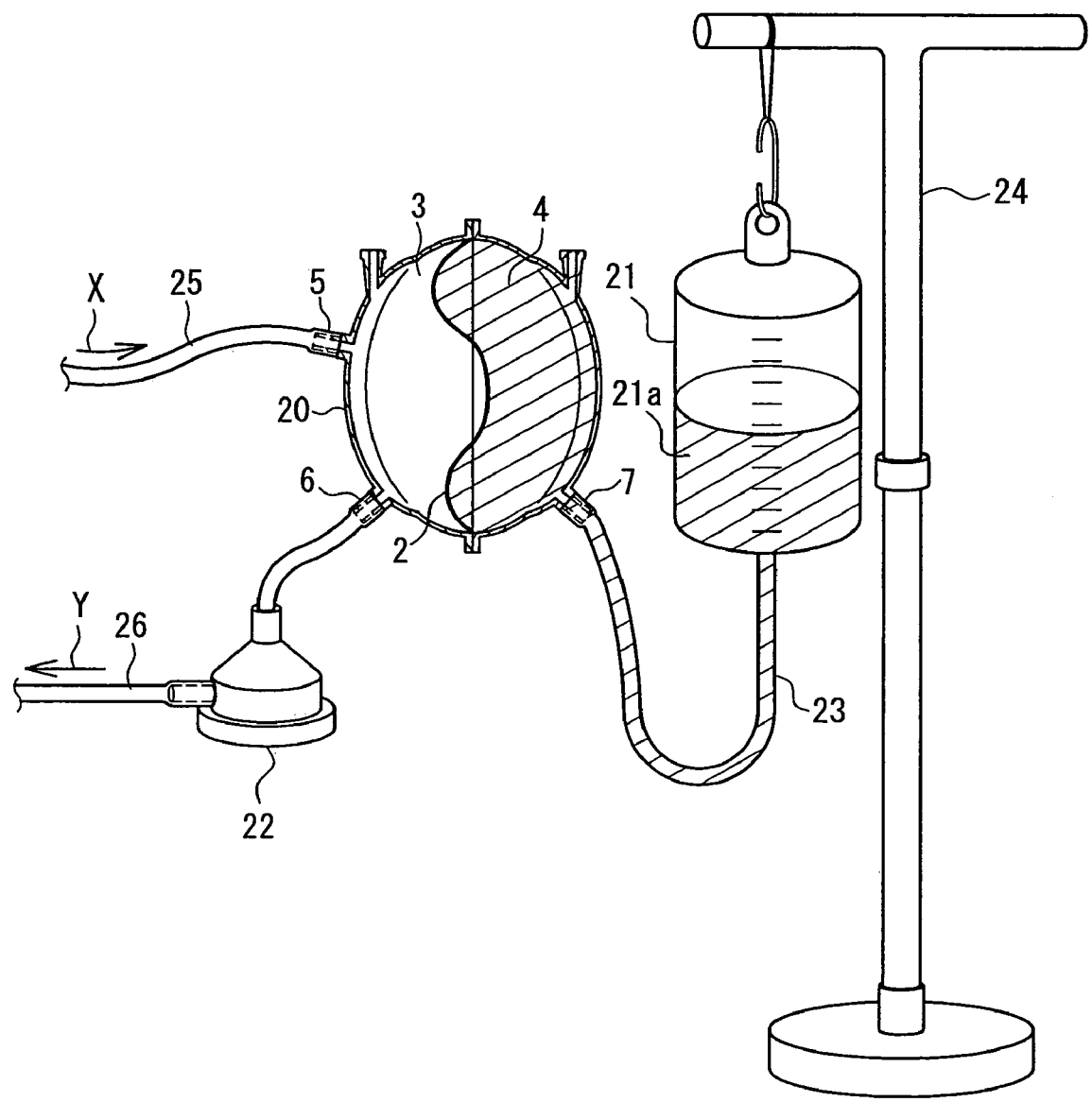
FIG. 8 is a perspective view showing an action of the extracorporeal blood circulating apparatus when starting blood removal and during the blood removal.

Next, operational processes and actions when starting blood removal and during the blood removal will be described with reference to FIG. 8. The clamp 27 is removed from the state shown in FIG. 7, and then the adjusting liquid 21a can be transferred from the volume adjusting chamber 4 to the adjusting liquid tank 21, by a pressure difference between the blood removal part of the living body and the adjusting liquid tank 21. As a result, the septum member 2 is moved by blood that is removed from the living body and flows into the blood storage chamber 3, thereby increasing the capacity of the blood storage chamber 3. During the extracorporeal blood circulation, a position of the septum member 2 is changed in accordance with an internal pressure on the extracorporeal circulation system, thereby adjusting the capacity of the blood storage chamber 3 automatically. The height of the volume adjusting chamber 4 is set in accordance with an estimated pressure of the blood on the extracorporeal circulation system and a target value of the capacity of the blood storage chamber 3, but may be adjusted as appropriate during the extracorporeal blood circulation.

Figure 9A:
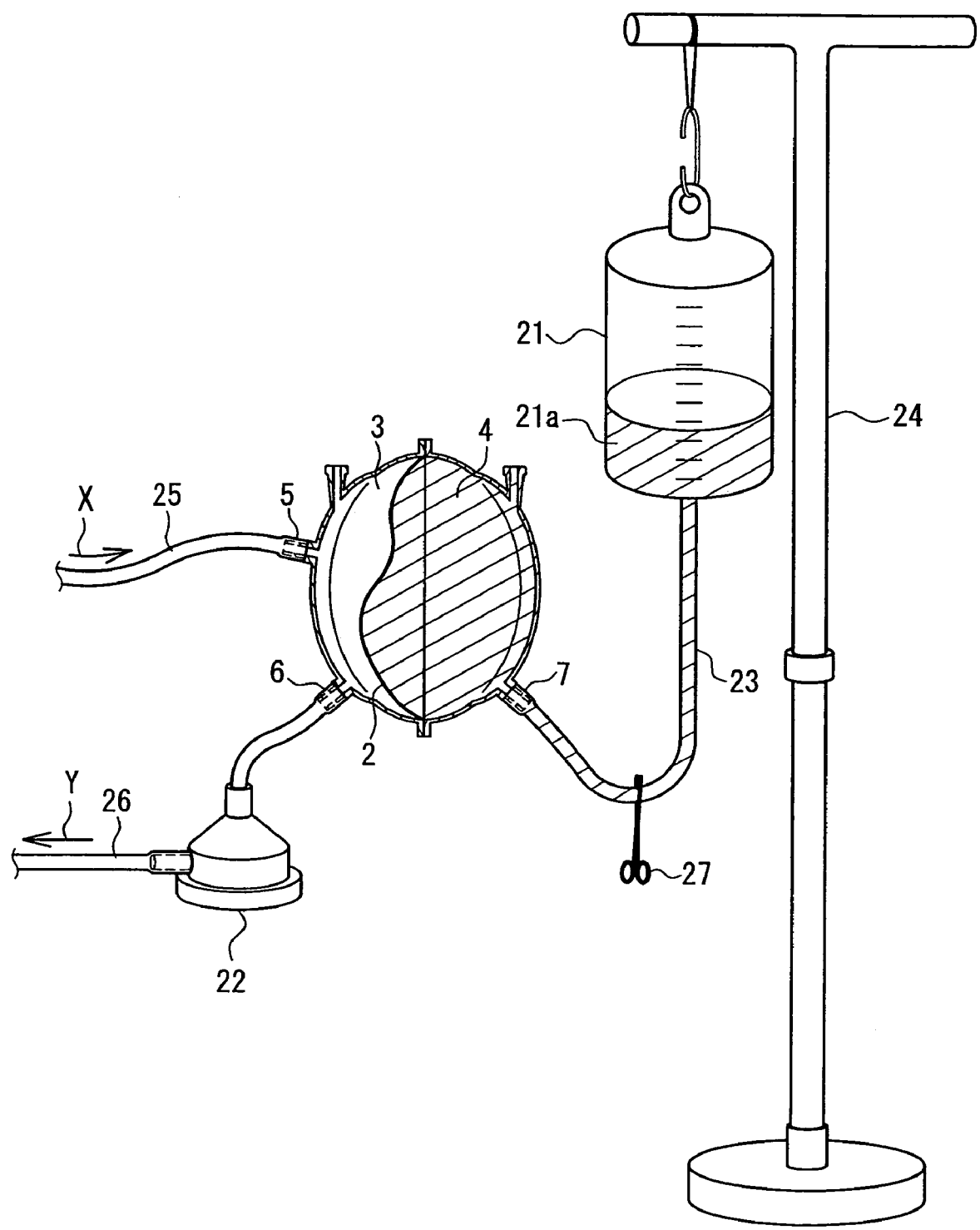
FIG. 9A is a perspective view showing an operational process of the extracorporeal blood circulating apparatus when increasing a capacity of a heart.
Figure 9B:
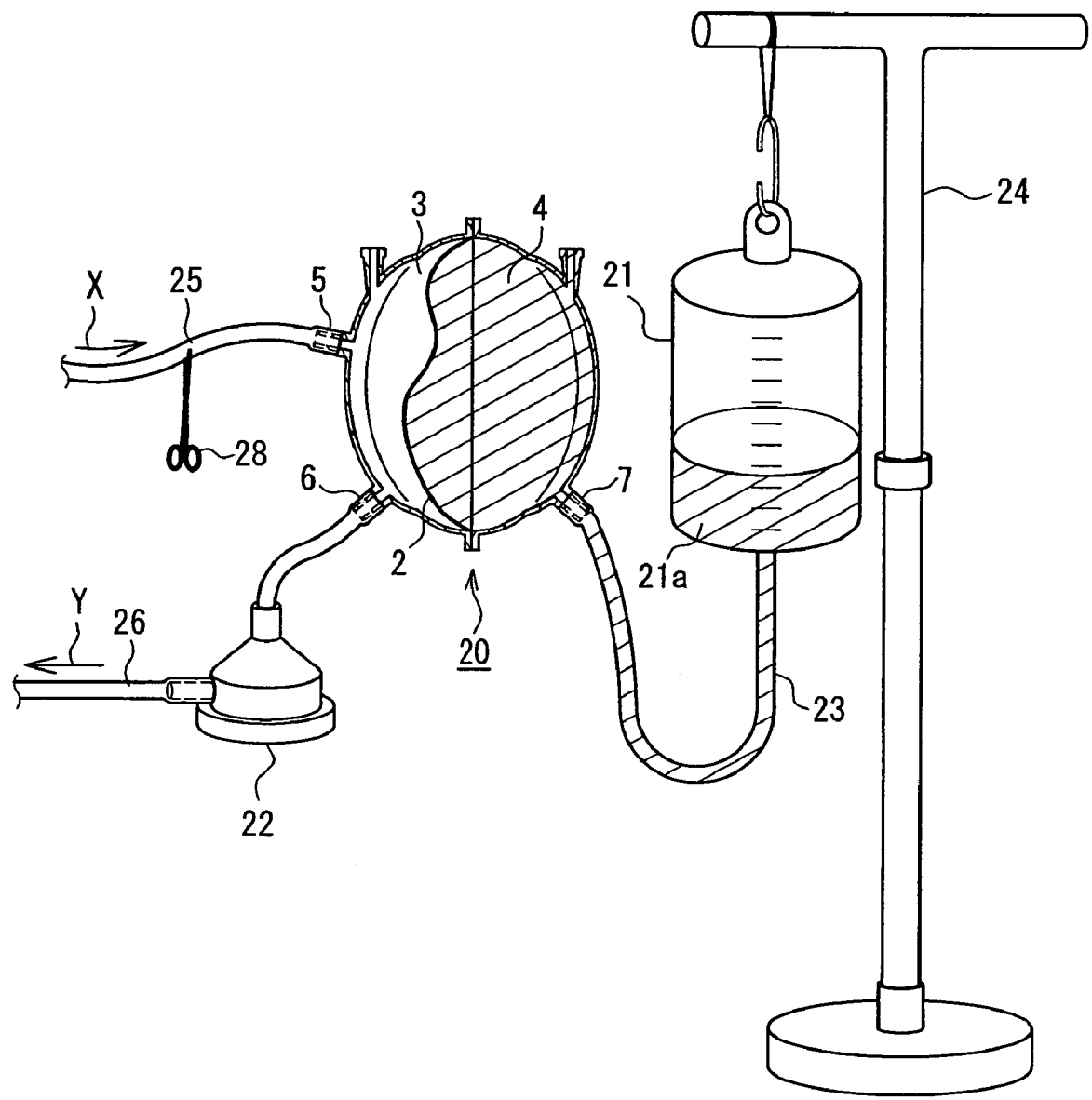
FIG. 9B is a perspective view showing other operational process of the extracorporeal blood circulating apparatus when increasing the capacity of the heart.

Next, adjustment processes for increasing a capacity of a heart of a living body will be described with reference to FIGS. 9A and 9B. FIGS. 9A and 9B respectively show the cases of operating with different methods.

In the case of the method shown in FIG. 9A, firstly, the adjusting liquid tank 21 is disposed in a high position so as to transfer the adjusting liquid 21a into the volume adjusting chamber 4, in a state where the clamp 27 is not used (not shown in the figure). The septum member 2 is moved toward the blood storage chamber 3 side in accordance with an amount of the adjusting liquid 21a to be transferred, thereby decreasing the volume of the blood storage chamber 3. As a result, the blood stored in the blood storage chamber 3 is ejected from the venous reservoir 20, and returns into the body, thereby increasing the capacity of the heart. When the blood storage chamber 3 is set to have an appropriate capacity, the state thereof is maintained by blocking the adjusting path tube 23 with the damp 27.

In the case of the method shown in FIG. 9B, a part of the blood removal-side tube 25 is narrowed by the clamp 28 so as to decrease a channel cross-sectional area. Thereby, a pressure in the blood storage chamber 3 is decreased, whereby the adjusting liquid 21a is transferred from the adjusting liquid tank 21 into the volume adjusting chamber 4. The septum member 2 is moved toward the blood storage chamber 3 side in accordance with an amount of the adjusting liquid 21a transferred, thereby decreasing the volume of the blood storage chamber 3. As a result, the blood stored in the blood storage chamber 3 is ejected from the venous reservoir 20, and returns into the body, thereby increasing the capacity of the heart. In the case where the blood removal-side tube evacuates the blood removal part of the living body, it can be solved by increasing the capacity of the heart as described above. When the blood storage chamber 3 is set to have an appropriate capacity, the state thereof is maintained by blocking the adjusting path tube 23 by the clamp, which is not shown in the figure though.

Figure 10:
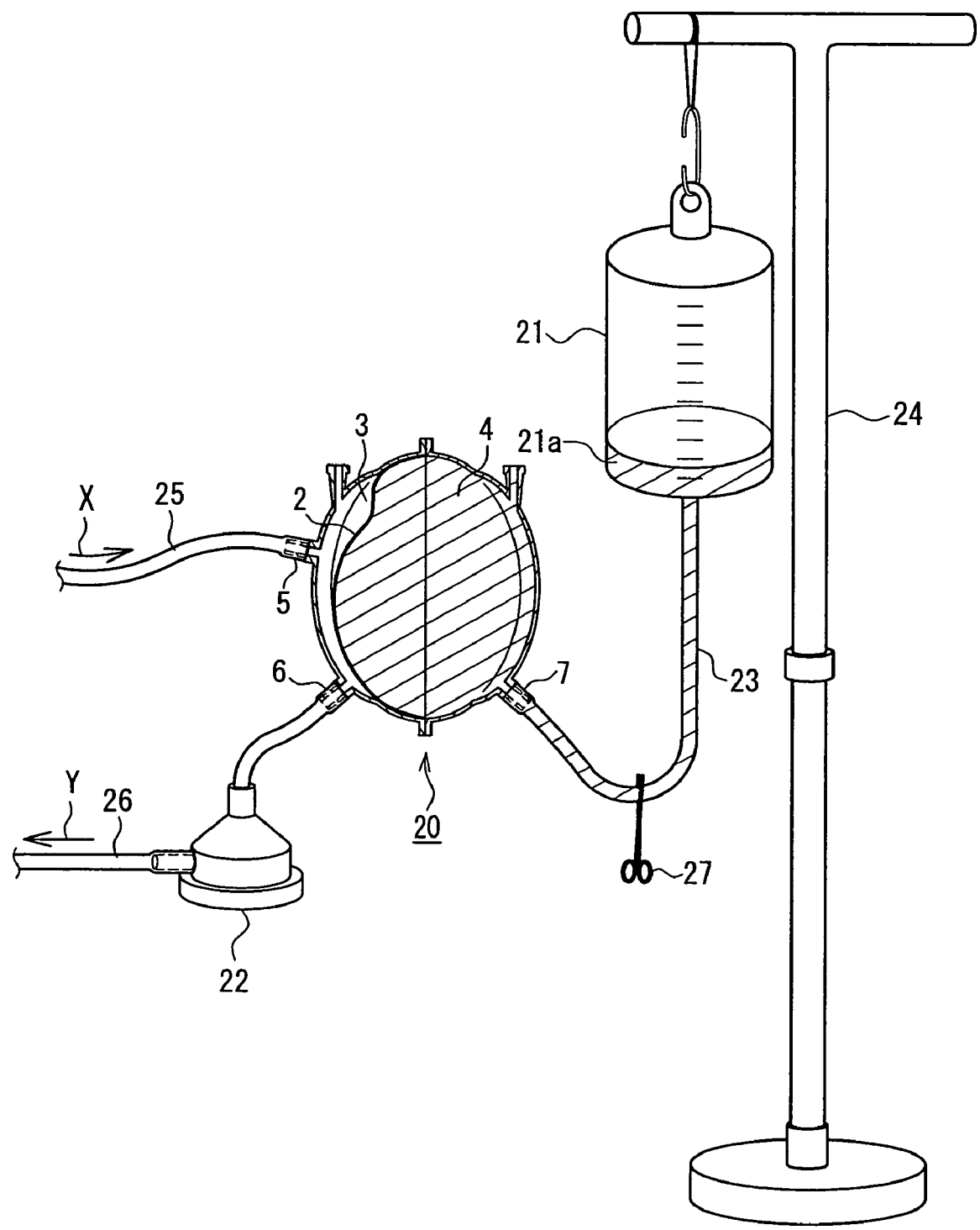
FIG. 10 is a perspective view showing an action of the extracorporeal blood circulating apparatus when being detached from the extracorporeal blood circulation.

Finally, operational processes and actions when being detached from the state of the extracorporeal blood circulation will be described with reference to FIG. 10. The adjusting liquid tank 21 is disposed in a high position so as to decrease a flowing amount of the blood pump 22. Thereby, the adjusting liquid 21a is transferred from the adjusting liquid tank 21 into the volume adjusting chamber 4, and the septum member 2 is moved toward the blood storage chamber 3 side so as to decrease the volume of the blood storage chamber 3. In this state, the adjusting path tube 23 is blocked by the damp 27, and then the extracorporeal blood circulation is terminated.

Figure 11:
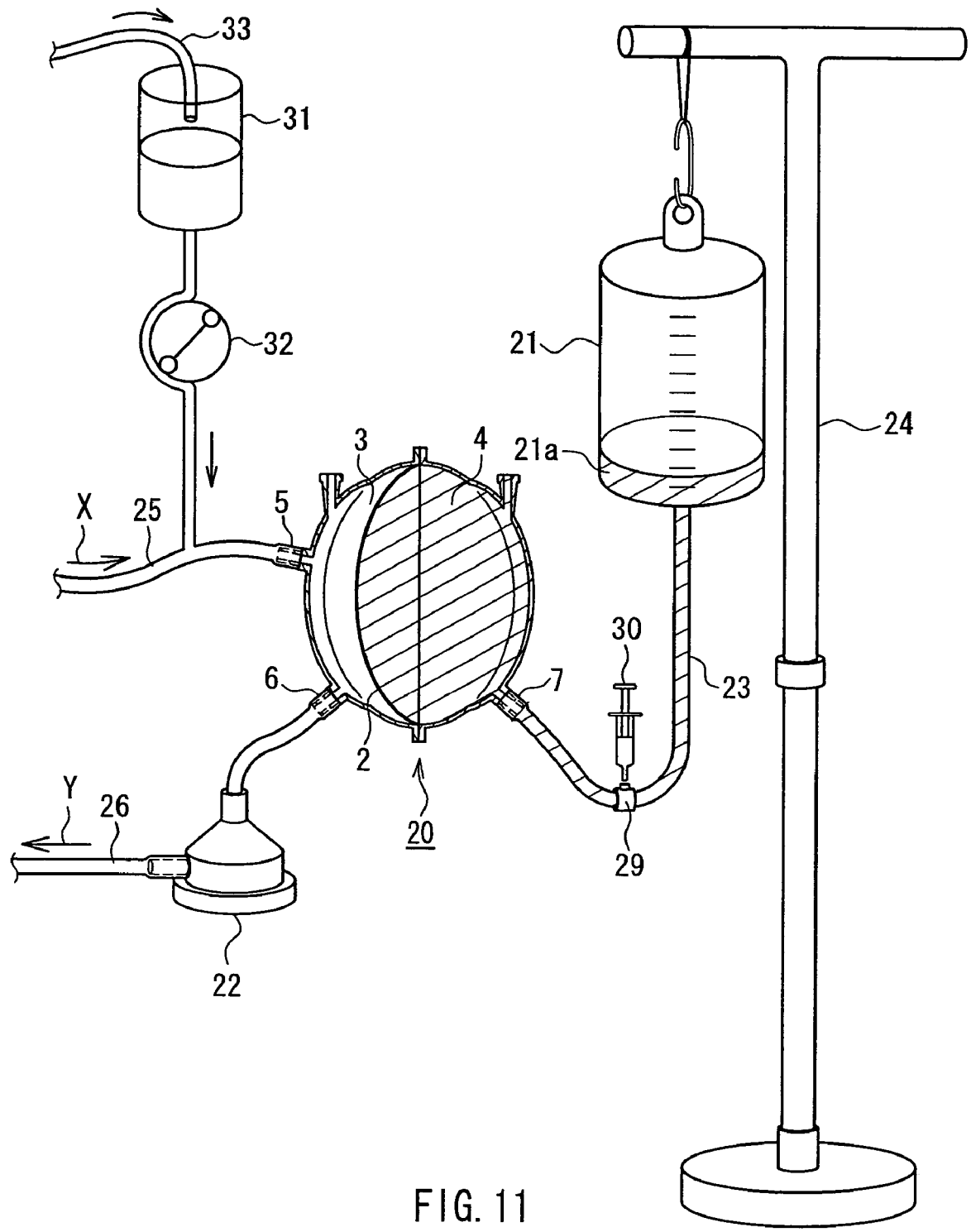
FIG. 11 is a perspective view showing a configuration of the extracorporeal blood circulating apparatus to which other element is added.

FIG. 11 is a perspective view showing an extracorporeal blood circulating apparatus that is constructed by adding further elements to the extracorporeal blood circulating apparatus with the above-described configuration.

A first additional element is a fine-adjusting port 29 provided for the adjusting path tube 23. The adjusting liquid 21a can be injected and ejected by a syringe 30 via the fine-adjusting port 29, thereby fine-adjusting a filling amount of the adjusting liquid 21a in the volume adjusting chamber 4.

A second additional element is an auxiliary circulation system including an auxiliary venous reservoir 31 and a pump 32. The auxiliary venous reservoir 31, which is shown in a simplified manner, is a typical open-type venous reservoir. To the auxiliary venous reservoir 31, an auxiliary system tube 33 is connected for collecting blood that is removed from parts other than the blood removal part of the living body. The auxiliary venous reservoir 31 is connected to the inflow port 5 of the closed-type venous reservoir 20 via the pump 32, and blood stored in the. auxiliary venous reservoir 31 is supplied into the closed-type venous reservoir 20.

The above-described embodiment has the configuration where the inflow and outflow of the adjusting liquid 21a are carried out by changing the height of the adjusting liquid tank 21 and accordingly changing a difference in height, but it also is possible to employ a configuration where the inflow and outflow of the adjusting liquid 21a between the adjusting liquid tank 21 and the volume adjusting chamber 4 are carried out by using the pump so as to increase and decrease the volume of the blood storage chamber 3. In the latter case, it is required that, during the extracorporeal blood circulation, the adjusting liquid 21a can be transferred freely between the adjusting liquid tank 21 and the volume adjusting chamber 4, and the height of the position of the adjusting liquid tank 21 can be set appropriately.

Since the volume adjusting chamber 4 is separated from the blood storage chamber 3 by the septum member 2, blood is not contaminated. Thus, it is not required to sterilize the adjusting liquid 21a to be filled in the volume adjusting chamber 4, however, considering a rare case where the septum member 2 is broken, it is preferable to use a sterilized isotonic solution such as a physiological saline solution.

The septum member 2 preferably is made of a material that has flexibility, pressure resistance and excellent processibility, and for example, films of PVC, polyolefin, polytetrafluoroethylene and the like can be used.

INDUSTRIAL APPLICABILITY

According to the present invention, an extracorporeal blood circulation that can control a blood storage amount to be most appropriate and can adjust easily can be obtained throughout all steps from before starting an extracorporeal blood circulation to terminating it, and thus can be applied usefully to an extracorporeal blood circulating apparatus.

The invention claimed is:

1. An extracorporeal blood circulating apparatus comprising:
    a closed-type venous reservoir having a blood storage chamber for storing blood and a volume adjusting chamber for storing an adjusting liquid for volume adjustment that are disposed adjacently by partitioning a closed space formed by a housing with a flexible septum member;
    an adjusting liquid tank for storing the adjusting liquid that is connected to the volume adjusting chamber; and
    a blood pump that is connected to the blood storage chamber,
    the housing being provided with an inflow port for allowing blood to inflow and an outflow port for allowing blood to outflow that respectively communicate with the blood storage chamber, and an adjusting port for injecting and ejecting the adjusting liquid that communicates with the volume adjusting chamber,
    the blood pump being connected to the blood storage chamber via the outflow port,
    the adjusting liquid tank being connected to the volume adjusting chamber via the adjusting port,
    wherein
    the apparatus is provided with a supporting unit that holds the adjusting liquid tank so that a height of the adjusting liquid tank is variable,
    the adjusting liquid tank and the adjusting port are connected by a conduit member having a configuration that can adjust a flowing amount, and configured such that
    when the height of the adjusting liquid tank is changed, in accordance with a change in a relative height of the adjusting liquid tank with respect to the closed type venous reservoir, an amount of the adjusting liquid stored in the volume adjusting chamber is varied based on a difference in height, thereby the septum member being deformed in the housing so as to vary the volume of the blood storage chamber.

2. The extracorporeal blood circulating apparatus according to claim 1, wherein the conduit member is made of a flexible tube.

3. The extracorporeal blood circulating apparatus according to claim 1, wherein the conduit member comprises a channel adjusting portion for changing a channel cross-sectional area in a channel.

4. The extracorporeal blood circulating apparatus according to claim 1, comprising a measuring portion for measuring an amount of the adjusting liquid that is stored in the adjusting liquid tank.

5. The extracorporeal blood circulating apparatus according to claim 1, wherein the closed-type venous reservoir comprises:
    a first blockade avoiding channel forming a space bulging outward that is provided on an inner wall surface of the housing at a part facing the blood storage chamber; and
    the inflow port and the outflow port that respectively are disposed so as to communicate with the first blockade avoiding channel.

6. The extracorporeal blood circulating apparatus according to claim 1, comprising a fine-adjusting port for injecting and ejecting the adjusting liquid between the adjusting port and the adjusting liquid tank.

7. The extracorporeal blood circulating apparatus according to claim 1, comprising:
    an auxiliary venous reservoir for collecting blood that is removed from parts other than a blood removal part of a living body; and
    a blood ejecting device for allowing the blood that is stored in the auxiliary venous reservoir to inflow into the inflow port of the closed-type venous reservoir.

8. A closed-type venous reservoir comprising:
    a housing forming a closed space;
    a blood storage chamber for storing blood and a volume adjusting chamber for storing an adjusting liquid for volume adjustment that are disposed adjacently by partitioning the closed space;
    an inflow port for allowing blood to inflow and an outflow port for allowing blood to outflow that are provided at the housing so as to communicate with the blood storage chamber; and
    an adjusting port for injecting and ejecting the adjusting liquid that is provided at the housing so as to communicate with the volume adjusting chamber,
    wherein
    the closed space is partitioned by a flexible septum member into the blood storage chamber and the volume adjusting chamber,
    a first blockade avoiding channel forming a space bulging outward is provided on an inner wall surface of the housing at a part facing the blood storage chamber; and
    the inflow port and the outflow port are disposed so as to communicate with the first blockade avoiding channel.

9. The closed-type venous reservoir according to claim 8, wherein
    a second blockade avoiding channel forming a space bulging outward is provided on the inner wall surface of the housing at a part facing the volume adjusting chamber, and
    the adjusting port is disposed so as to communicate with the second blockade avoiding channel.

10. The closed-type venous reservoir according to claim 8, wherein an air vent port is provided so as to communicate with the first blockade avoiding channel.

11. The closed-type venous reservoir according to claim 8, wherein a gas-liquid separator membrane that encloses the inflow port and the air vent port so as to separate the inflow port and the air vent port from the blood storage chamber is disposed at a part where the inflow port is connected to the blood storage chamber.

12. The closed-type venous reservoir according to claim 8, wherein a pressure measuring port is provided so as to communicate with the second blockade avoiding channel.

13. The closed-type venous reservoir according to claim 8, wherein the first blockade avoiding channel is formed into a groove shape along the housing.

14. An extracorporeal blood circulating method comprising:
    using the extracorporeal blood circulating apparatus according to claim 1;
    connecting the inflow port of the closed-type venous reservoir to a blood removal part of an living body directly or via another member;
    connecting an outlet of the blood pump to an autotransfusing part of the living body directly or via another member;

filling a system comprising the adjusting liquid tank, the conduit and the volume adjusting chamber with the adjusting liquid;

adjusting a filling amount of the adjusting liquid in the volume adjusting chamber by adjusting a height of the adjusting liquid tank with respect to the closed-type venous reservoir so that the blood storage chamber has a blood storage capacity appropriate for priming before starting the extracorporeal blood circulation;

closing a channel of the conduit member after completing the adjustment so as to start the priming by operating the blood pump; and releasing the channel of the conduit member and holding the adjusting liquid tank in a position, with respect to the blood removal part of the living body, that is lower than a height of the adjusting liquid tank during the priming so as to start blood removal, after completing the priming.

15. The extracorporeal blood circulating method according to claim 14, further comprising:

using a flexible tube as the conduit member; and closing the channel of the conduit member by narrowing a bore of the tube by a clamp.

16. The extracorporeal blood circulating method according to claim 14, further comprising changing the height of the adjusting liquid tank to be in a higher position with respect to the blood removal part of the living body so as to increase a blood storage capacity of a heart of the living body, during the blood removal.

17. The extracorporeal blood circulating method according to claim 14, further comprising decreasing a cross-sectional area of a channel that connects the inflow port of the closed-type venous reservoir and the blood removal part of the living body, so as to increase a capacity of a heart of the living body, during the blood removal.

18. The extracorporeal blood circulating method according to claim 14, further comprising:

decreasing the height of the adjusting liquid tank with respect to the living body to be lower than the height of the adjusting liquid tank during the blood removal so as to decrease a volume of the blood storage chamber to be sufficient for maintaining a cross-sectional area of a blood channel;

operating the blood pump in a state of decreasing a discharging amount; and thereafter terminating the extracorporeal blood circulation.

19. The extracorporeal blood circulating method according to claim 14, further comprising:

providing a fine-adjusting port for injecting and ejecting the adjusting liquid between the adjusting port and the adjusting liquid tank; and injecting and ejecting the adjusting liquid by using a syringe via the fine-adjusting port so as to fine-adjust a filling amount of the adjusting liquid in the volume adjusting chamber.

* * * * *